(12) United States Patent
Uriarte

(10) Patent No.: US 11,273,296 B2
(45) Date of Patent: Mar. 15, 2022

(54) TATTOO MACHINE

(71) Applicant: Jorge Uriarte, Irvine, CA (US)

(72) Inventor: Jorge Uriarte, Irvine, CA (US)

( * ) Notice: Subject to any disclaimer, the term of this patent is extended or adjusted under 35 U.S.C. 154(b) by 260 days.

(21) Appl. No.: 16/653,739

(22) Filed: Oct. 15, 2019

(65) Prior Publication Data

US 2021/0106801 A1 Apr. 15, 2021

(51) Int. Cl.
*A61M 37/00* (2006.01)

(52) U.S. Cl.
CPC ................ *A61M 37/0076* (2013.01)

(58) Field of Classification Search
CPC .......... A61M 37/0076; A61M 37/0084; A01K 11/00; A01K 11/005; A61B 2017/3409; A61B 90/10; A61B 90/11
USPC ........................................................ 606/185
See application file for complete search history.

(56) References Cited

U.S. PATENT DOCUMENTS

| | | |
|---|---|---|
| 4,602,798 A | 7/1986 | Wettstein |
| 5,242,360 A | 9/1993 | Bayer |
| 6,341,831 B1* | 1/2002 | Weber .................. A01K 11/005 347/1 |
| 2007/0028722 A1 | 2/2007 | Vecchi |
| 2009/0209992 A1 | 8/2009 | McConchie |
| 2015/0352346 A1 | 12/2015 | Webb |
| 2016/0106516 A1 | 4/2016 | Mesallum |
| 2016/0263365 A1* | 9/2016 | Smith ............... A61M 37/0076 |
| 2018/0000419 A1 | 1/2018 | Rassman |

* cited by examiner

*Primary Examiner* — Diane D Yabut
*Assistant Examiner* — Brigid K Byrd
(74) *Attorney, Agent, or Firm* — Ariel Bentolila

(57) ABSTRACT

A tattoo machine is disclosed herein. The tattoo machine comprises at least one brace for supporting the machine on a body part. A base carriage is supported on the brace and is displaceable along a length of the brace. A top carrier is hingeably coupled to the base carriage. A holder plate is displaceably coupled to the top carrier, wherein the displacement of the holder plate within the top carriage is facilitated in a direction along the length of the holder plate. A tattoo applicator is supported at a free end of the holder plate, wherein the tattoo applicator comprises a ball for housing a tip of a needle. One aspect of the tattoo machine is that the depth at which the tattoo applicator operated on a body part is manually adjustable.

20 Claims, 6 Drawing Sheets

TATTOO MACHINE

COPYRIGHT NOTICE

A portion of the disclosure of this patent document contains material that is subject to copyright protection by the author thereof. The copyright owner has no objection to the facsimile reproduction by anyone of the patent document or patent disclosure for the purposes of referencing as patent prior art, as it appears in the Patent and Trademark Office, patent file or records, but otherwise reserves all copyright rights whatsoever.

BACKGROUND OF THE RELEVANT PRIOR ART

One or more embodiments of the invention generally relate to a tattoo machine. More particularly, certain embodiments of the invention relate to a CNC tattoo machine in which CNC controlled motors are configured to control the movement of an applicator along the X and Y axes.

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon. CNC controlled tattoo machines are known in the art which are configured to apply a tattoo on a body part of a user in accordance with an input program fed to the machine. Such machines typically include a frame in which a user can insert or place a body part on which the user wishes to have the tattoo done. The body part can be securely supported on the frame by means of straps or other similar means. An applicator of the tattoo machine is also supported on the frame such that the applicator can be moved thereon, wherein the movement of the applicator is governed by the input program fed to the CNC controlled tattoo machine and depends upon the design of the tattoo that the user desires.

The following is an example of a specific aspect in the prior art that, while expected to be helpful to further educate the reader as to additional aspects of the prior art, is not to be construed as limiting the present invention, or any embodiments thereof, to anything stated or implied therein or inferred thereupon. By way of educational background, another aspect of the prior art generally useful to be aware of is that the conventional CNC controlled tattoo machines have the applicator configured to move on the frame of the machine along the X, Y, and Z axes. Typically, the movement of the applicator along the X, Y, and Z axes are facilitated via CNC controlled motors. Typically, two axes, e.g., X and Y axes define an XY plane that forms the plane of reference for the surface area of the user's body part on which the applicator moves per the design of the tattoo. The contours of the body part are, therefore, measured along the remaining Z axis. Measurement of the contours of the body part is performed to compute the locations where the applicator needs to be lifted as well as the height by which the applicator needs to be lifted to optimally apply the tattoo without causing any injuries to the user. Some conventional CNC controlled machines include a handheld switch that allows the user to stop the operation of the machine, in case of discomfort or injuries arising due to incorrect or inaccurate reading along the Z-axis, which causes the inaccurate movement of the applicator on the user's body part.

In view of the foregoing, it is clear that these traditional techniques are not perfect and leave room for more optimal approaches.

BRIEF DESCRIPTION OF THE DRAWINGS

The present invention is illustrated by way of example, and not by way of limitation, in the figures of the accompanying drawings and in which like reference numerals refer to similar elements and in which.

Figure 1:
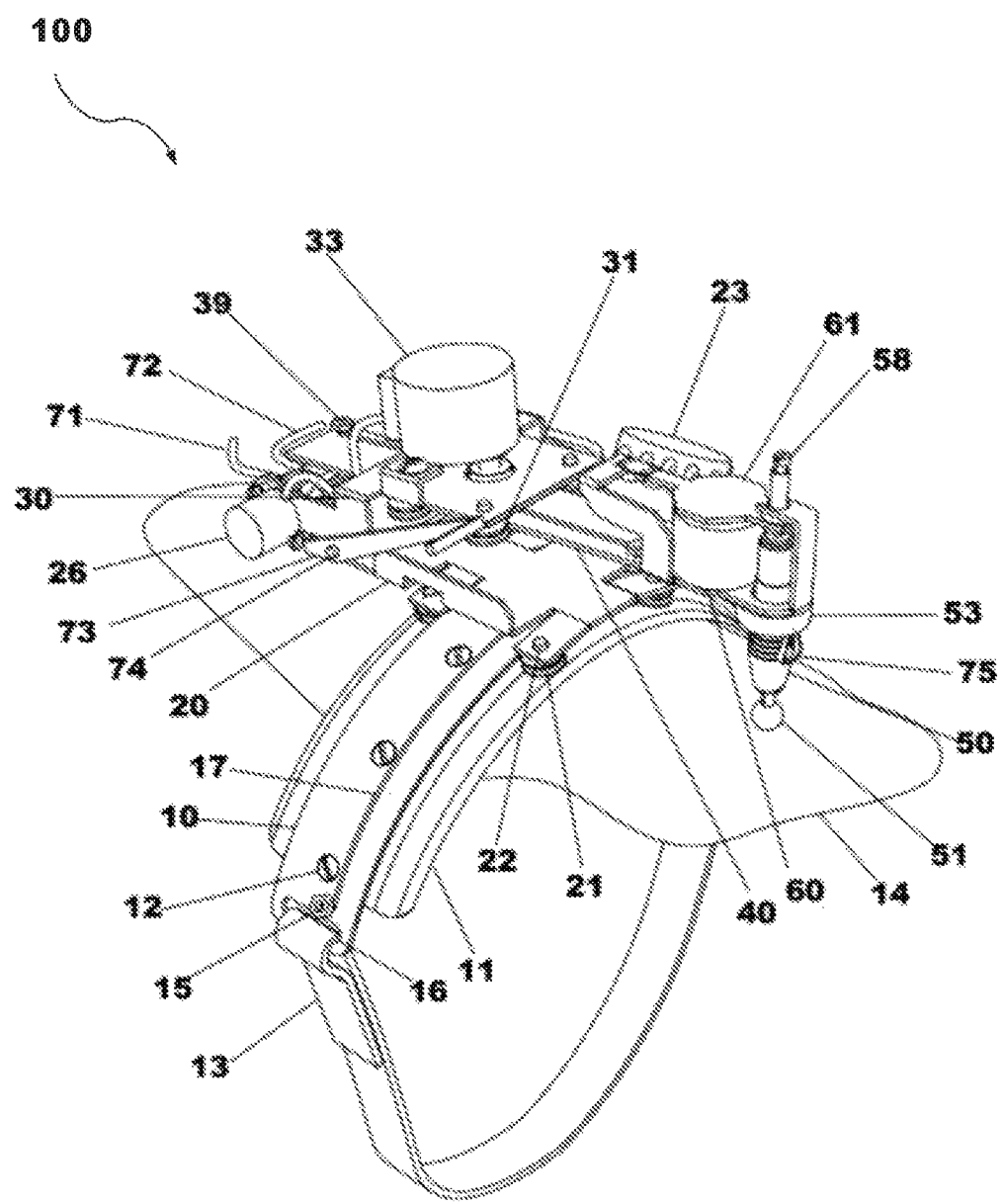
FIG. 1 and FIG. 2 illustrate isometric views of a CNC controlled tattoo machine, in accordance with an embodiment of the present invention.

Unless otherwise indicated illustrations in the figures are not necessarily drawn to scale.

DETAILED DESCRIPTION OF SOME EMBODIMENTS

The present invention is best understood by reference to the detailed figures and description set forth herein.

Embodiments of the invention are discussed below with reference to the Figures. However, those skilled in the art will readily appreciate that the detailed description given herein with respect to these figures is for explanatory purposes as the invention extends beyond these limited embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

It is to be further understood that the present invention is not limited to the particular methodology, compounds, materials, manufacturing techniques, uses, and applications, described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

All words of approximation as used in the present disclosure and claims should be construed to mean "approximate," rather than "perfect," and may accordingly be employed as a meaningful modifier to any other word, specified parameter, quantity, quality, or concept. Words of approximation, include, yet are not limited to terms such as "substantial", "nearly", "almost", "about", "generally", "largely", "essentially", "closely approximate", etc.

As will be established in some detail below, it is well settled law, as early as 1939, that words of approximation are not indefinite in the claims even when such limits are not defined or specified in the specification.

For example, see Ex parte Mallory, 52 USPQ 297, 297 (Pat. Off. Bd. App. 1941) where the court said "The examiner has held that most of the claims are inaccurate because apparently the laminar film will not be entirely eliminated. The claims specify that the film is "substantially" eliminated and for the intended purpose, it is believed that the slight portion of the film which may remain is negligible. We are of the view, therefore, that the claims may be regarded as sufficiently accurate."

Note that claims need only "reasonably apprise those skilled in the art" as to their scope to satisfy the definiteness requirement. See Energy Absorption Sys., Inc. v. Roadway Safety Servs., Inc., Civ. App. 96-1264, slip op. at 10 (Fed. Cir. Jul. 3, 1997) (unpublished) Hybridtech v. Monoclonal Antibodies, Inc., 802 F.2d 1367, 1385, 231 USPQ 81, 94 (Fed. Cir. 1986), cert. denied, 480 U.S. 947 (1987). In addition, the use of modifiers in the claim, like "generally" and "substantial," does not by itself render the claims indefinite. See Seattle Box Co. v. Industrial Crating & Packing, Inc., 731 F.2d 818, 828-29, 221 USPQ 568, 575-76 (Fed. Cir. 1984).

Moreover, the ordinary and customary meaning of terms like "substantially" includes "reasonably close to: nearly, almost, about", connoting a term of approximation. See In re Frye, Appeal No. 2009-006013, 94 USPQ2d 1072, 1077, 2010 WL 889747 (B.P.A.I. 2010) Depending on its usage, the word "substantially" can denote either language of approximation or language of magnitude. Deering Precision Instruments, L.L.C. v. Vector Distribution Sys., Inc., 347 F.3d 1314, 1323 (Fed. Cir. 2003) (recognizing the "dual ordinary meaning of th[e] term ["substantially"] as connoting a term of approximation or a term of magnitude"). Here, when referring to the "substantially halfway" limitation, the Specification uses the word "approximately" as a substitute for the word "substantially" (Fact 4). (Fact 4). The ordinary meaning of "substantially halfway" is thus reasonably close to or nearly at the midpoint between the forwardmost point of the upper or outsole and the rearwardmost point of the upper or outsole.

Similarly, the term 'substantially' is well recognized in case law to have the dual ordinary meaning of connoting a term of approximation or a term of magnitude. See Dana Corp. v. American Axle & Manufacturing, Inc., Civ. App. 04-1116, 2004 U.S. App. LEXIS 18265,*13-14 (Fed. Cir. Aug. 27, 2004) (unpublished). The term "substantially" is commonly used by claim drafters to indicate approximation. See Cordis Corp. v. Medtronic AVE Inc., 339 F.3d 1352, 1360 (Fed. Cir. 2003) ("The patents do not set out any numerical standard by which to determine whether the thickness of the wall surface is 'substantially uniform.' The term 'substantially,' as used in this context, denotes approximation. Thus, the walls must be of largely or approximately uniform thickness."); see also Deering Precision Instruments, LLC v. Vector Distribution Sys., Inc., 347 F.3d 1314, 1322 (Fed. Cir. 2003); Epcon Gas Sys., Inc. v. Bauer Compressors, Inc., 279 F.3d 1022, 1031 (Fed. Cir. 2002). We find that the term "substantially" was used in just such a manner in the claims of the patents-in-suit: "substantially uniform wall thickness" denotes a wall thickness with approximate uniformity.

It should also be noted that such words of approximation as contemplated in the foregoing clearly limits the scope of claims such as saying 'generally parallel' such that the adverb 'generally' does not broaden the meaning of parallel. Accordingly, it is well settled that such words of approximation as contemplated in the foregoing (e.g., like the phrase 'generally parallel') envisions some amount of deviation from perfection (e.g., not exactly parallel), and that such words of approximation as contemplated in the foregoing are descriptive terms commonly used in patent claims to avoid a strict numerical boundary to the specified parameter. To the extent that the plain language of the claims relying on such words of approximation as contemplated in the foregoing are clear and uncontradicted by anything in the written description herein or the figures thereof, it is improper to rely upon the present written description, the figures, or the prosecution history to add limitations to any of the claim of the present invention with respect to such words of approximation as contemplated in the foregoing. That is, under such circumstances, relying on the written description and prosecution history to reject the ordinary and customary meanings of the words themselves is impermissible. See, for example, Liquid Dynamics Corp. v. Vaughan Co., 355 F.3d 1361, 69 USPQ2d 1595, 1600-01 (Fed. Cir. 2004). The plain language of phrase 2 requires a "substantial helical flow." The term "substantial" is a meaningful modifier implying "approximate," rather than "perfect." In Cordis Corp. v. Medtronic AVE, Inc., 339 F.3d 1352, 1361 (Fed. Cir. 2003), the district court imposed a precise numeric constraint on the term "substantially uniform thickness." We noted that the proper interpretation of this term was "of largely or approximately uniform thickness" unless something in the prosecution history imposed the "clear and unmistakable disclaimer" needed for narrowing beyond this simple-language interpretation. Id. In Anchor Wall Systems v. Rockwood Retaining Walls, Inc., 340 F.3d 1298, 1311 (Fed. Cir. 2003)" Id. at 1311. Similarly, the plain language of claim 1 requires neither a perfectly helical flow nor a flow that returns precisely to the center after one rotation (a limitation that arises only as a logical consequence of requiring a perfectly helical flow).

The reader should appreciate that case law generally recognizes a dual ordinary meaning of such words of approximation, as contemplated in the foregoing, as connoting a term of approximation or a term of magnitude; e.g., see Deering Precision Instruments, L.L.C. v. Vector Distrib. Sys., Inc., 347 F.3d 1314, 68 USPQ2d 1716, 1721 (Fed. Cir. 2003), cert. denied, 124 S. Ct. 1426 (2004) where the court was asked to construe the meaning of the term "substantially" in a patent claim. Also see Epcon, 279 F.3d at 1031 ("The phrase 'substantially constant' denotes language of approximation, while the phrase 'substantially below' signifies language of magnitude, i.e., not insubstantial."). Also, see, e.g., Epcon Gas Sys., Inc. v. Bauer Compressors, Inc., 279 F.3d 1022 (Fed. Cir. 2002) (construing the terms "substantially constant" and "substantially below"); Zodiac Pool Care, Inc. v. Hoffinger Indus., Inc., 206 F.3d 1408 (Fed. Cir. 2000) (construing the term "substantially inward"); York Prods., Inc. v. Cent. Tractor Farm & Family Ctr., 99 F.3d 1568 (Fed. Cir. 1996) (construing the term "substantially the entire height thereof"); Tex. Instruments Inc. v. Cypress Semiconductor Corp., 90 F.3d 1558 (Fed. Cir. 1996) (construing the term "substantially in the common plane"). In conducting their analysis, the court instructed to begin with the ordinary meaning of the claim terms to one of ordinary skill in the art. Prima Tek, 318 F.3d at 1148. Reference to dictionaries and our cases indicates that the term "substantially" has numerous ordinary meanings. As the district court stated, "substantially" can mean "significantly" or "considerably." The term "substantially" can also mean "largely" or "essentially." Webster's New 20th Century Dictionary 1817 (1983).

Words of approximation, as contemplated in the foregoing, may also be used in phrases establishing approximate ranges or limits, where the end points are inclusive and approximate, not perfect; e.g., see AK Steel Corp. v. Sollac, 344 F.3d 1234, 68 USPQ2d 1280, 1285 (Fed. Cir. 2003) where it where the court said [W]e conclude that the ordinary meaning of the phrase "up to about 10%" includes the "about 10%" endpoint. As pointed out by AK Steel, when an object of the preposition "up to" is nonnumeric, the most natural meaning is to exclude the object (e.g., painting the wall up to the door). On the other hand, as pointed out by Sollac, when the object is a numerical limit, the normal meaning is to include that upper numerical limit (e.g., counting up to ten, seating capacity for up to seven passengers). Because we have here a numerical limit—"about 10%"—the ordinary meaning is that that endpoint is included.

In the present specification and claims, a goal of employment of such words of approximation, as contemplated in the foregoing, is to avoid a strict numerical boundary to the modified specified parameter, as sanctioned by Pall Corp. v. Micron Separations, Inc., 66 F.3d 1211, 1217, 36 USPQ2d 1225, 1229 (Fed. Cir. 1995) where it states "It is well established that when the term "substantially" serves reasonably to describe the subject matter so that its scope would be understood by persons in the field of the invention, and to distinguish the claimed subject matter from the prior art, it is not indefinite." Likewise see Verve LLC v. Crane Cams Inc., 311 F.3d 1116, 65 USPQ2d 1051, 1054 (Fed. Cir. 2002). Expressions such as "substantially" are used in patent documents when warranted by the nature of the invention, in order to accommodate the minor variations that may be appropriate to secure the invention. Such usage may well satisfy the charge to "particularly point out and distinctly claim" the invention, 35 U.S.C. § 112, and indeed may be necessary in order to provide the inventor with the benefit of his invention. In Andrew Corp. v. Gabriel Elecs. Inc., 847 F.2d 819, 821-22, 6 USPQ2d 2010, 2013 (Fed. Cir. 1988) the court explained that usages such as "substantially equal" and "closely approximate" may serve to describe the invention with precision appropriate to the technology and without intruding on the prior art. The court again explained in Ecolab Inc. v. Envirochem, Inc., 264 F.3d 1358, 1367, 60 USPQ2d 1173, 1179 (Fed. Cir. 2001) that "like the term 'about,' the term 'substantially' is a descriptive term commonly used in patent claims to 'avoid a strict numerical boundary to the specified parameter, see Ecolab Inc. v. Envirochem Inc., 264 F.3d 1358, 60 USPQ2d 1173, 1179 (Fed. Cir. 2001) where the court found that the use of the term "substantially" to modify the term "uniform" does not render this phrase so unclear such that there is no means by which to ascertain the claim scope.

Similarly, other courts have noted that like the term "about," the term "substantially" is a descriptive term commonly used in patent claims to "avoid a strict numerical boundary to the specified parameter."; e.g., see Pall Corp. v. Micron Seps., 66 F.3d 1211, 1217, 36 USPQ2d 1225, 1229 (Fed. Cir. 1995); see, e.g., Andrew Corp. v. Gabriel Elecs. Inc., 847 F.2d 819, 821-22, 6 USPQ2d 2010, 2013 (Fed. Cir. 1988) (noting that terms such as "approach each other," "close to," "substantially equal," and "closely approximate" are ubiquitously used in patent claims and that such usages, when serving reasonably to describe the claimed subject matter to those of skill in the field of the invention, and to distinguish the claimed subject matter from the prior art, have been accepted in patent examination and upheld by the courts). In this case, "substantially" avoids the strict 100% nonuniformity boundary.

Indeed, the foregoing sanctioning of such words of approximation, as contemplated in the foregoing, has been established as early as 1939, see Ex parte Mallory, 52 USPQ 297, 297 (Pat. Off. Bd. App. 1941) where, for example, the court said "the claims specify that the film is "substantially" eliminated and for the intended purpose, it is believed that the slight portion of the film which may remain is negligible. We are of the view, therefore, that the claims may be regarded as sufficiently accurate." Similarly, In re Hutchison, 104 F.2d 829, 42 USPQ 90, 93 (C.C.P.A. 1939) the court said "It is realized that "substantial distance" is a relative and somewhat indefinite term, or phrase, but terms and phrases of this character are not uncommon in patents in cases where, according to the art involved, the meaning can be determined with reasonable clearness."

Hence, for at least the forgoing reason, Applicants submit that it is improper for any examiner to hold as indefinite any claims of the present patent that employ any words of approximation.

Unless defined otherwise, all technical and scientific terms used herein have the same meanings as commonly understood by one of ordinary skill in the art to which this invention belongs. Preferred methods, techniques, devices, and materials are described, although any methods, techniques, devices, or materials similar or equivalent to those described herein may be used in the practice or testing of the present invention. Structures described herein are to be understood also to refer to functional equivalents of such structures. The present invention will be described in detail below with reference to embodiments thereof as illustrated in the accompanying drawings.

References to a "device," an "apparatus," a "system," etc., in the preamble of a claim should be construed broadly to mean "any structure meeting the claim terms" exempt for any specific structure(s)/type(s) that has/(have) been explicitly disavowed or excluded or admitted/implied as prior art in the present specification or incapable of enabling an object/aspect/goal of the invention. Furthermore, where the present specification discloses an object, aspect, function, goal, result, or advantage of the invention that a specific prior art structure and/or method step is similarly capable of performing yet in a very different way, the present invention disclosure is intended to and shall also implicitly include and cover additional corresponding alternative embodiments that are otherwise identical to that explicitly disclosed except that they exclude such prior art structure(s)/step(s), and shall accordingly be deemed as providing sufficient disclosure to support a corresponding negative limitation in a claim claiming such alternative embodiment(s), which exclude such very different prior art structure(s)/step(s)/way(s).

From reading the present disclosure, other variations and modifications will be apparent to persons skilled in the art. Such variations and modifications may involve equivalent and other features which are already known in the art, and which may be used instead of or in addition to features already described herein.

Although Claims have been formulated in this Application to particular combinations of features, it should be understood that the scope of the disclosure of the present invention also includes any novel feature or any novel combination of features disclosed herein either explicitly or implicitly or any generalization thereof, whether or not it relates to the same invention as presently claimed in any Claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable subcombination. The Applicants hereby give notice that new Claims may be formulated to such features and/or combinations of such features during the prosecution of the present Application or of any further Application derived therefrom.

References to "one embodiment," "an embodiment," "example embodiment," "various embodiments," "some embodiments," "embodiments of the invention," etc., may indicate that the embodiment(s) of the invention so described may include a particular feature, structure, or characteristic, but not every possible embodiment of the invention necessarily includes the particular feature, structure, or characteristic. Further, repeated use of the phrase "in one embodiment," or "in an exemplary embodiment," "an embodiment," do not necessarily refer to the same embodiment, although they may. Moreover, any use of phrases like "embodiments" in connection with "the invention" are never meant to characterize that all embodiments of the invention must include the particular feature, structure, or characteristic, and should instead be understood to mean "at least some embodiments of the invention" include the stated particular feature, structure, or characteristic.

References to "user", or any similar term, as used herein, may mean a human or non-human user thereof. Moreover, "user", or any similar term, as used herein, unless expressly stipulated otherwise, is contemplated to mean users at any stage of the usage process, to include, without limitation, direct user(s), intermediate user(s), indirect user(s), and end user(s). The meaning of "user", or any similar term, as used herein, should not be otherwise inferred or induced by any pattern(s) of description, embodiments, examples, or referenced prior-art that may (or may not) be provided in the present patent.

References to "end user", or any similar term, as used herein, is generally intended to mean late stage user(s) as opposed to early stage user(s). Hence, it is contemplated that there may be a multiplicity of different types of "end user" near the end stage of the usage process. Where applicable, especially with respect to distribution channels of embodiments of the invention comprising consumed retail products/services thereof (as opposed to sellers/vendors or Original Equipment Manufacturers), examples of an "end user" may include, without limitation, a "consumer", "buyer", "customer", "purchaser", "shopper", "enjoyer", "viewer", or individual person or non-human thing benefiting in any way, directly or indirectly, from use of. or interaction, with some aspect of the present invention.

In some situations, some embodiments of the present invention may provide beneficial usage to more than one stage or type of usage in the foregoing usage process. In such cases where multiple embodiments targeting various stages of the usage process are described, references to "end user", or any similar term, as used therein, are generally intended to not include the user that is the furthest removed, in the foregoing usage process, from the final user therein of an embodiment of the present invention.

Where applicable, especially with respect to retail distribution channels of embodiments of the invention, intermediate user(s) may include, without limitation, any individual person or non-human thing benefiting in any way, directly or indirectly, from use of, or interaction with, some aspect of the present invention with respect to selling, vending, Original Equipment Manufacturing, marketing, merchandising, distributing, service providing, and the like thereof.

References to "person", "individual", "human", "a party", "animal", "creature", or any similar term, as used herein, even if the context or particular embodiment implies living user, maker, or participant, it should be understood that such characterizations are sole by way of example, and not limitation, in that it is contemplated that any such usage, making, or participation by a living entity in connection with making, using, and/or participating, in any way, with embodiments of the present invention may be substituted by such similar performed by a suitably configured non-living entity, to include, without limitation, automated machines, robots, humanoids, computational systems, information processing systems, artificially intelligent systems, and the like. It is further contemplated that those skilled in the art will readily recognize the practical situations where such living makers, users, and/or participants with embodiments of the present invention may be in whole, or in part, replaced with such non-living makers, users, and/or participants with embodiments of the present invention. Likewise, when those skilled in the art identify such practical situations where such living makers, users, and/or participants with embodiments of the present invention may be in whole, or in part, replaced with such non-living makers, it will be readily apparent in light of the teachings of the present invention how to adapt the described embodiments to be suitable for such non-living makers, users, and/or participants with embodiments of the present invention. Thus, the invention is thus to also cover all such modifications, equivalents, and alternatives falling within the spirit and scope of such adaptations and modifications, at least in part, for such non-living entities.

Headings provided herein are for convenience and are not to be taken as limiting the disclosure in any way.

The enumerated listing of items does not imply that any or all of the items are mutually exclusive, unless expressly specified otherwise.

It is understood that the use of specific component, device and/or parameter names are for example only and not meant to imply any limitations on the invention. The invention may thus be implemented with different nomenclature/terminology utilized to describe the mechanisms/units/structures/components/devices/parameters herein, without limitation. Each term utilized herein is to be given its broadest interpretation given the context in which that term is utilized.

Terminology. The following paragraphs provide definitions and/or context for terms found in this disclosure (including the appended claims):

"Comprising" And "contain" and variations of them—Such terms are open-ended and mean "including but not limited to". When employed in the appended claims, this term does not foreclose additional structure or steps. Consider a claim that recites: "A memory controller comprising a system cache . . . ." Such a claim does not foreclose the memory controller from including additional components (e.g., a memory channel unit, a switch).

"Configured To." Various units, circuits, or other components may be described or claimed as "configured to" perform a task or tasks. In such contexts, "configured to" or "operable for" is used to connote structure by indicating that the mechanisms/units/circuits/components include structure (e.g., circuitry and/or mechanisms) that performs the task or tasks during operation. As such, the mechanisms/unit/circuit/component can be said to be configured to (or be operable) for perform(ing) the task even when the specified mechanisms/unit/circuit/component is not currently operational (e.g., is not on). The mechanisms/units/circuits/components used with the "configured to" or "operable for" language include hardware—for example, mechanisms, structures, electronics, circuits, memory storing program instructions executable to implement the operation, etc. Reciting that a mechanism/unit/circuit/component is "configured to" or "operable for" perform(ing) one or more tasks is expressly intended not to invoke 35 U.S.C..sctn.112, sixth paragraph, for that mechanism/unit/circuit/component. "Configured to" may also include adapting a manufacturing process to fabricate devices or components that are adapted to implement or perform one or more tasks.

"Based On." As used herein, this term is used to describe one or more factors that affect a determination. This term does not foreclose additional factors that may affect a determination. That is, a determination may be solely based on those factors or based, at least in part, on those factors. Consider the phrase "determine A based on B." While B may be a factor that affects the determination of A, such a phrase does not foreclose the determination of A from also being based on C. In other instances, A may be determined based solely on B.

The terms "a", "an" and "the" mean "one or more", unless expressly specified otherwise.

All terms of exemplary language (e.g., including, without limitation, "such as", "like", "for example", "for instance", "similar to", etc.) are not exclusive of any other, potentially, unrelated, types of examples; thus, implicitly mean "by way of example, and not limitation . . . ", unless expressly specified otherwise.

Unless otherwise indicated, all numbers expressing conditions, concentrations, dimensions, and so forth used in the specification and claims are to be understood as being modified in all instances by the term "about." Accordingly, unless indicated to the contrary, the numerical parameters set forth in the following specification and attached claims are approximations that may vary depending at least upon a specific analytical technique.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phase "consisting essentially of" and "consisting of" limits the scope of a claim to the specified elements or method steps, plus those that do not materially affect the basis and novel characteristic(s) of the claimed subject matter (see Norian Corp. v Stryker Corp., 363 F.3d 1321, 1331-32, 70 USPQ2d 1508, Fed. Cir. 2004). Moreover, for any claim of the present invention which claims an embodiment "consisting essentially of" or "consisting of" a certain set of elements of any herein described embodiment it shall be understood as obvious by those skilled in the art that the present invention also covers all possible varying scope variants of any described embodiment(s) that are each exclusively (i.e., "consisting essentially of") functional subsets or functional combination thereof such that each of these plurality of exclusive varying scope variants each consists essentially of any functional subset(s) and/or functional combination(s) of any set of elements of any described embodiment(s) to the exclusion of any others not set forth therein. That is, it is contemplated that it will be obvious to those skilled how to create a multiplicity of alternate embodiments of the present invention that simply consisting essentially of a certain functional combination of elements of any described embodiment(s) to the exclusion of any others not set forth therein, and the invention thus covers all such exclusive embodiments as if they were each described herein.

With respect to the terms "comprising," "consisting of," and "consisting essentially of," where one of these three terms is used herein, the disclosed and claimed subject matter may include the use of either of the other two terms. Thus in some embodiments not otherwise explicitly recited, any instance of "comprising" may be replaced by "consisting of" or, alternatively, by "consisting essentially of", and thus, for the purposes of claim support and construction for "consisting of" format claims, such replacements operate to create yet other alternative embodiments "consisting essentially of" only the elements recited in the original "comprising" embodiment to the exclusion of all other elements.

Moreover, any claim limitation phrased in functional limitation terms covered by 35 USC § 112(6) (post AIA 112(f)) which has a preamble invoking the closed terms "consisting of," or "consisting essentially of," should be understood to mean that the corresponding structure(s) disclosed herein define the exact metes and bounds of what the so claimed invention embodiment(s) consists of, or consisting essentially of, to the exclusion of any other elements which do not materially affect the intended purpose of the so claimed embodiment(s).

Devices or system modules that are in at least general communication with each other need not be in continuous communication with each other, unless expressly specified otherwise. In addition, devices or system modules that are in at least general communication with each other may communicate directly or indirectly through one or more intermediaries. Moreover, it is understood that any system components described or named in any embodiment or claimed herein may be grouped or sub-grouped (and accordingly implicitly renamed) in any combination or sub-combination as those skilled in the art can imagine as suitable for the particular application, and still be within the scope and spirit of the claimed embodiments of the present invention. For an example of what this means, if the invention was a controller of a motor and a valve and the embodiments and claims articulated those components as being separately grouped and connected, applying the foregoing would mean that such an invention and claims would also implicitly cover the valve being grouped inside the motor and the controller being a remote controller with no direct physical connection to the motor or internalized valve, as such the claimed invention is contemplated to cover all ways of grouping and/or adding of intermediate components or systems that still substantially achieve the intended result of the invention.

A description of an embodiment with several components in communication with each other does not imply that all such components are required. On the contrary a variety of optional components are described to illustrate the wide variety of possible embodiments of the present invention.

As is well known to those skilled in the art many careful considerations and compromises typically must be made when designing for the optimal manufacture of a commercial implementation any system, and in particular, the embodiments of the present invention. A commercial implementation in accordance with the spirit and teachings of the present invention may configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

In the following description and claims, the terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

It is to be understood that any exact measurements/dimensions or particular construction materials indicated herein are solely provided as examples of suitable configurations and are not intended to be limiting in any way. Depending on the needs of the particular application, those skilled in the art will readily recognize, in light of the following teachings, a multiplicity of suitable alternative implementation details.

The present invention will now be described in detail with reference to embodiments thereof as illustrated in the accompanying drawings.

In accordance with an embodiment of the present invention, a CNC controlled tattoo machine includes two motors for controlling the movement of an applicator of the machine along X and Y axes. The movement of the applicator along the Z axis, in accordance with an embodiment of the present invention, is facilitated via a hinged support structure instead of a motor. An advantageous aspect of such a support structure is that such a support structure can be manually operable. More specifically, using such a hinged support structure, in accordance with some embodiments of the present invention, the contact of the applicator from the body part can be broken as per the will of the user instead of being controlled via the machine. This allows the user to, for example, repeatedly lift the applicator using the hinged support structure to either monitor the progress of the tattoo or just to relieve any sort of discomfort occurring during the tattooing operation.

Figure 2:
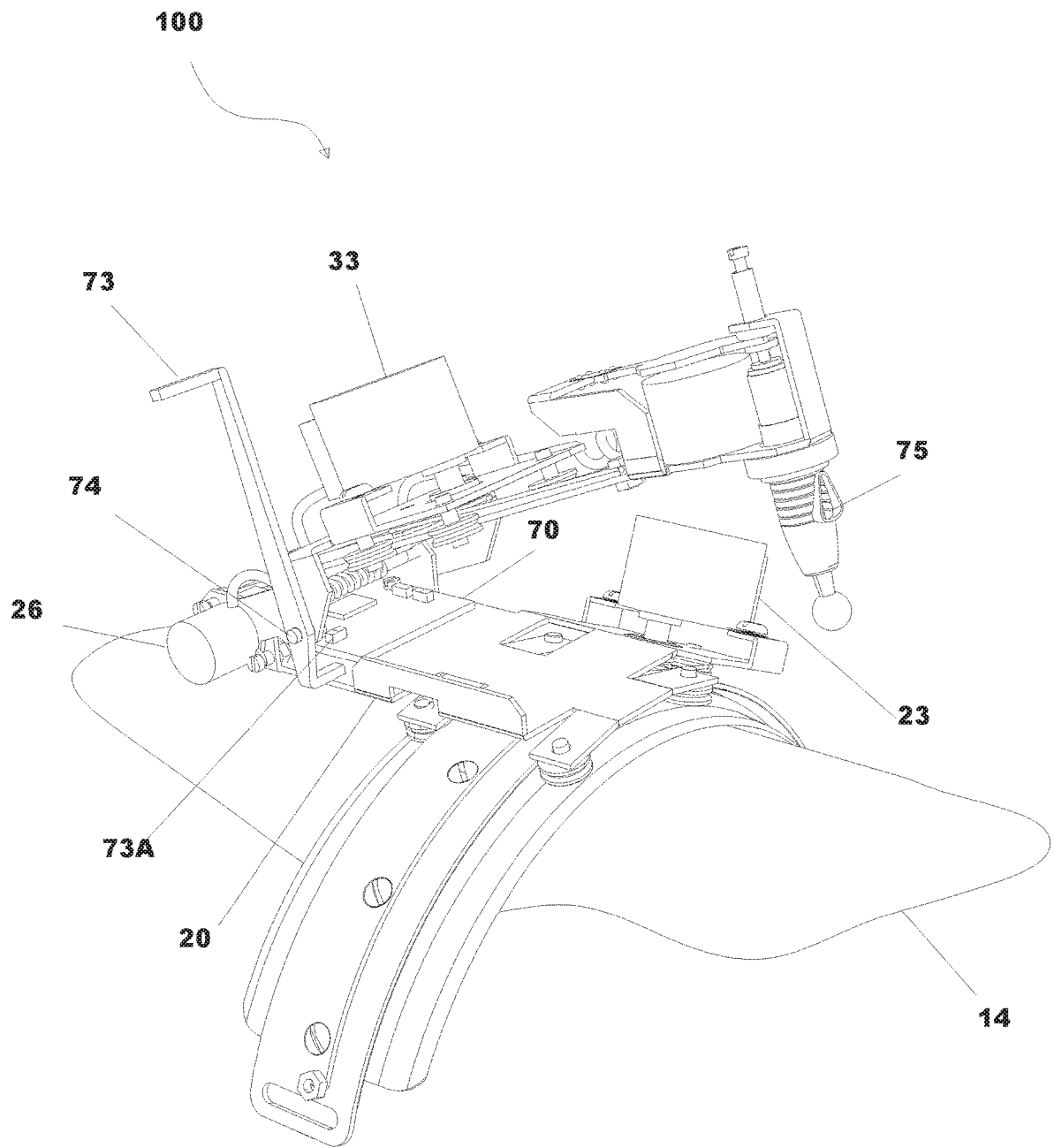

FIG. 1 and FIG. 2 illustrate isometric views of a CNC controlled tattoo machine 100 (hereinafter referred to as machine 100), in accordance with an embodiment of the present invention. Referring to FIG. 1, the machine 100 comprises a brace 10 that is fitted onto a body part 14. In accordance with an embodiment of the present invention, the brace 10 has a curved profile. In accordance with another embodiment, the brace 10 can have straight profile. More specifically, the profile of the brace 10 depends on the body part on which the tattoo is desired to be done and on the design of the tattoo as well. In some other embodiments, the brace 10 can be flexible. A cushioning pad 11 is provided on the brace 10 for the user's comfort. The cushioning pad 11 is fastened to the brace 10 by means of fasteners 12. In another embodiment, the cushioning pad 11 can be stuck onto the brace 10 using adhesives. The brace 10 comprises a loop 16 provided at each end thereof. The loop 16 facilitates the attachment of a strap 13, which is used to secure the machine 100 to the body part 14. In one embodiment, the strap 13 can have hook and loop fastening portions. In another embodiment, the strap 13 can have a buckle to secure to the body part 14. Other embodiments of the machine 100 can include multiple braces 10 and straps 13 for covering larger tattoo designs over larger tattooing areas on the body.

The machine 100 further comprises a base carriage 20. The base carriage 20 is supported on the brace 10 using pins 22. In another embodiment fasteners such as screws, nuts, and the like can be used for mounting the base carriage 20 on the brace 10. More specifically, the pins 22 support thereon grooved bearing wheels 21. The base carriage 20 is supported on the brace 10 using four pins 22 and four grooved bearing wheels 21. The grooved bearing wheels 21 have the grooved portion pressed against the edges of the brace 10 for facilitating the translation of the base carriage 20 along the length of the brace 10, wherein the length of the brace 10 defines a first axis, say X axis.

Figure 3A:
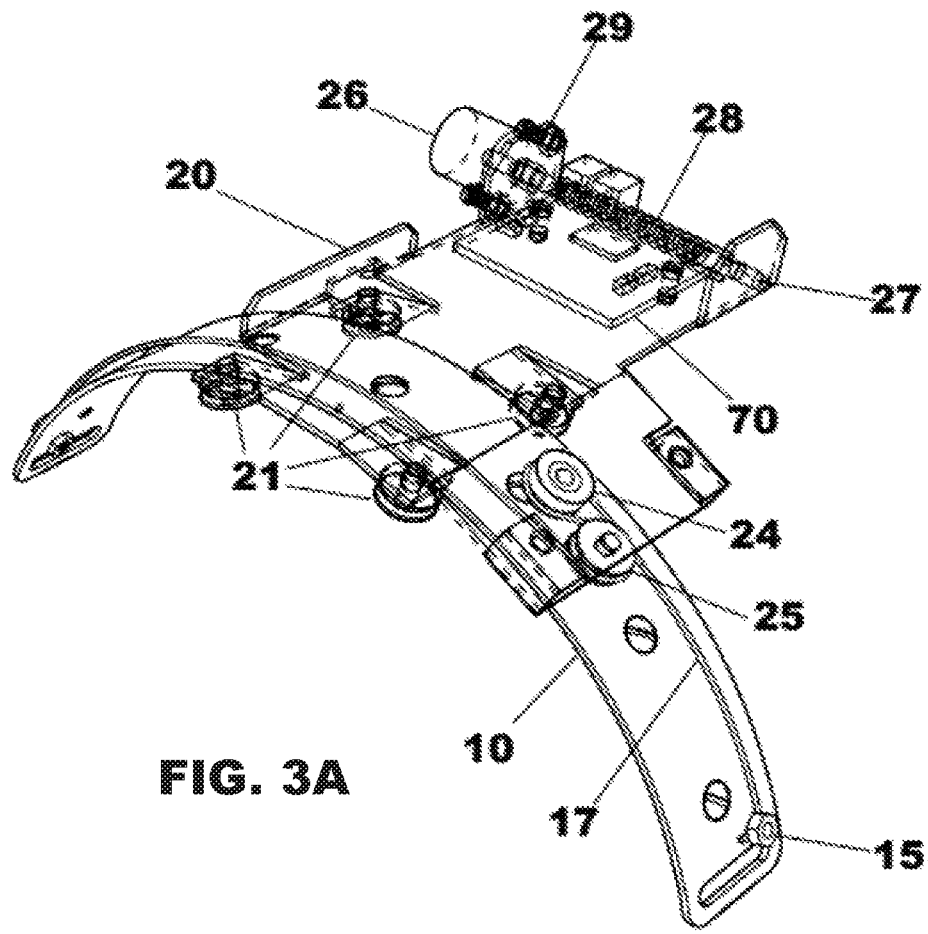
FIG. 3A and FIG. 3B illustrate isometric views depicting the brace with the base carriage assembled thereon, in accordance with an embodiment of the present invention.
Figure 3B:
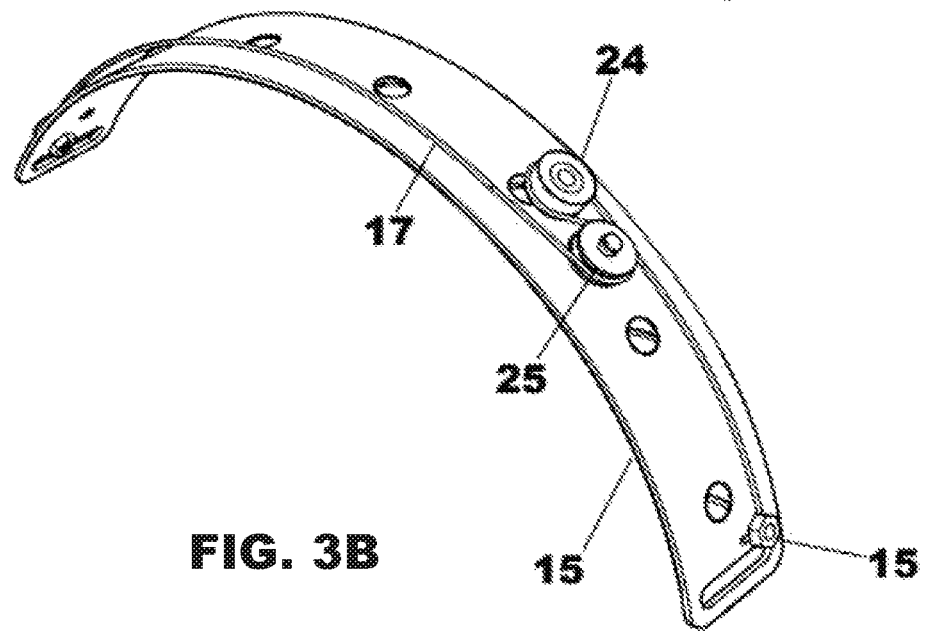

Referring to FIG. 2, the machine 100 comprises a first motor 23 that is supported on the base carriage 20. In one embodiment, the first motor 23 is a high torque stepper motor. The first motor 23 is provided on the base carriage 20 for facilitating the movement of the base carriage 20 along the length of the brace 10. FIG. 3A and FIG. 3B illustrate isometric views depicting the brace 10 with the base carriage 20 assembled thereon. Referring to FIG. 1 thru FIG. 3B, the machine 100 comprises a driving pulley 24 and an idler pulley 25 secured to the base carriage 20. A driving cable 17 is disposed on the brace 10 with the ends of the cable 17 being screwed or fastened to the brace 10 near the ends of the brace 10 via fasteners 15. The base carriage 20 is assembled on the brace 10 such that the cable 17 is received and wrapped around by the driving pulley 24 and the idler pulley 25. More specifically, the base carriage 20 is supported on the brace 10 via the grooved bearing wheels 21 as well as the fitment of the driving pulley 24 and the idler pulley 25 with the driving cable 17. The cushioning pad 11 has clearances to allow the grooved bearing wheels 21 to run freely along the length of brace 10. The fasteners 15 facilitate a taut fit of the driving cable 17 on the brace 10, thereby substantially reducing the chances of slippage driving cable 17 around the driving pulley 24. In an alternate embodiment, the driving pulley, the idler pulley, and the driving cable are replaced by sprockets and timing belts for facilitating the translation of the base carriage along the length of the brace 10. In another alternate embodiment, grooved bearing wheels 21 can be replaced by blocks made of engineering plastics.

In accordance with one embodiment of the present invention, the machine 100 comprises control printed circuit board (PCB) 70. In one embodiment, the motor 23 can be connected to and controlled via the control PCB 70. The motor 23 is coupled to the driving pulley 24 for facilitating the rotation of the driving pulley 24, wherein the rotation of the driving pulley 24 facilitates the linear movement of the base carriage 20 along the driving cable 17, and thus along the brace 10.

Figure 4:
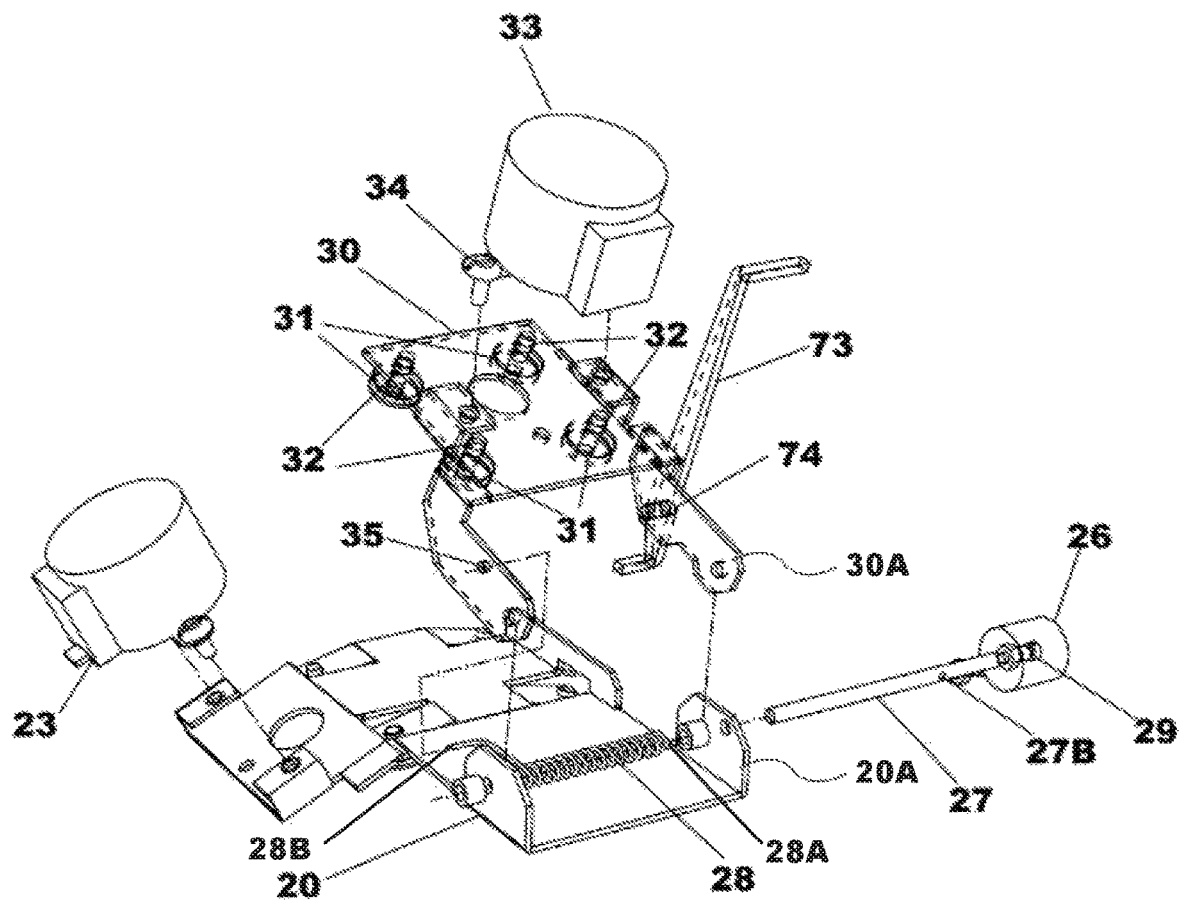
FIG. 4 illustrates an exploded view depicting the fitment of the top carrier on the base carriage, in accordance with an embodiment of the present invention.

Referring to FIG. 1 and FIG. 2, the machine 100 further comprises a top carrier 30, wherein the top carrier 30 has a holder plate 40 connected thereto. The top carrier 30 and the holder plate 40 are together supported on the base carriage 20. FIG. 4 illustrates an exploded view depicting the fitment of the top carrier 30 on the base carriage 20. Referring to FIG. 2 and FIG. 4, the base carriage 20 is hingeably connected with the top carrier 30. The hinged connection of the base carriage 20 and the top carrier 30 is facilitated by a shaft 27. The machine 100 further comprises a motor 26 secured to the base carriage 20 with screws 29 and a torsion spring 28. The shaft 27 functions as the hinge pin between the base carriage 20 and the top carrier 30. The top carrier 30 has brackets 30A which are aligned with and fitted in between brackets 20A of the base carriage 20. The shaft 27 is fitted into the aligned holes in the brackets 30A and the brackets 20A. The torsion spring 28 has a first end 28A and a second end 28B. The first end 28A of the torsion spring is secured to the shaft 27 at hole 27B configured on the shaft 27. The second end 28B of the torsion spring 28 is secured to a hole 35 configured on bracket 30A of the top carriage 30. The shaft 27 fitted between the base carriage 20 and the top carrier 30 facilitates the hingeable connection between the base carriage 20 and the top carrier 30, whereas the torsion spring 28 facilitates an application of constant pressure on the top carrier 30 and the holder plate 40, wherein the holder plate 40 has a tattoo applicator 50 mounted thereon. The application of the pressure on the holder plate 40 via the torsion spring 28 allows the tattoo applicator 50 to make a constant pressure contact with the tattooing area on the user's body. Furthermore, the motor 26 facilitates the variation of the pressure acting on the holder plate 40 and the tattoo applicator 50 mounted thereto by unwinding the torsion spring 28 to reduce the pressure or winding the torsion spring 28 to increase the pressure. In accordance with one embodiment, the motor 26 is controlled via the control PCB 70, and the control PCB 70 regulates the operation of the motor 26 in accordance with the input program specific to the tattoo design as well as the geometry of the tattooing area.

Figure 5A:
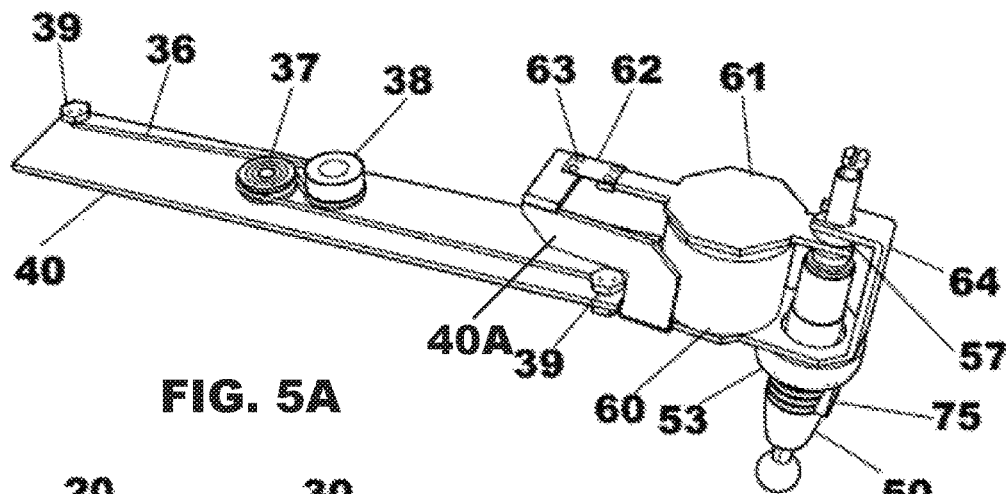
FIG. 5A and FIG. 5B illustrate isometric views of the holder plate being assembled on to the top carrier, in accordance with an embodiment of the present invention.
Figure 5B:
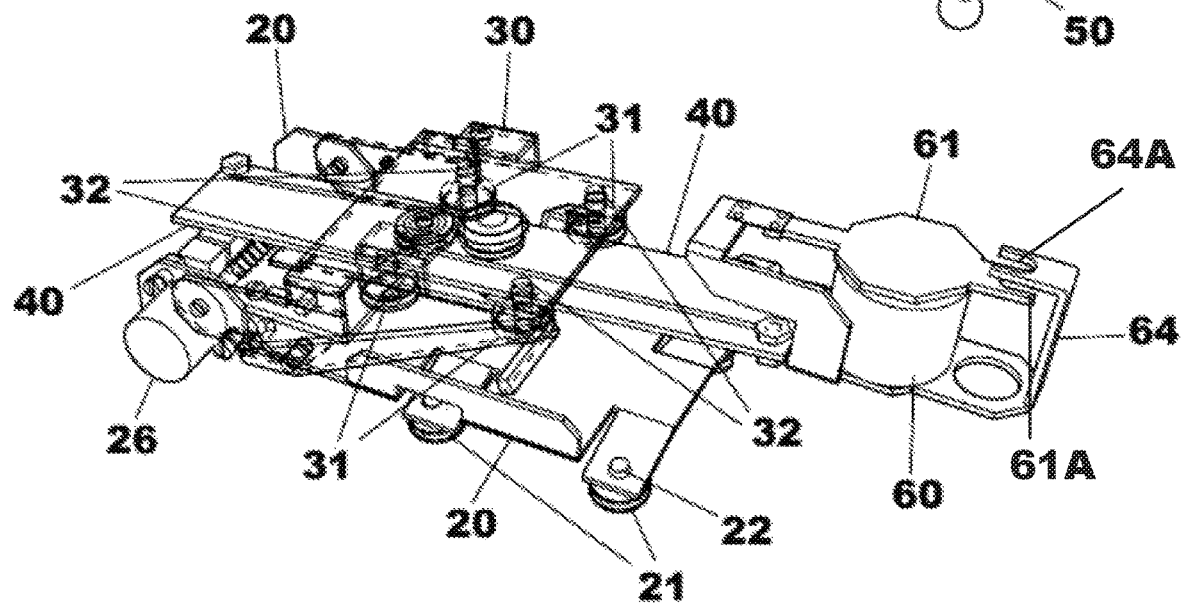

FIG. 5A and FIG. 5B illustrate isometric views of the holder plate 40 being assembled on to the top carrier 30, in accordance with an embodiment of the present invention. Referring to FIG. 4 thru FIG. 5B, the top carrier 30 comprises grooved bearing wheels 31 supported thereon by means of pins 32. In accordance with another embodiment, the grooved bearing wheels 31 can be supported on the top carrier via fasteners such as nut and screws, and the like. The holder plate 40 is held between the grooved bearing wheels 31. The grooved bearing wheels 31 facilitate the translation holder plate 40 between the grooved bearing wheels 31. The holder plate 40 comprises driving cable 36 that is disposed on the holder plate 40 and fastened to the ends of the holder plate 40 by means of fasteners 39. A driver pulley 38 and an idler pulley 39 are disposed on the holder plate 40, and the driving cable 36 is wrapped around the driver pulley 38 and the idler pulley 39. A motor 33 is coupled to the driver pulley 38 for facilitating the rotation of the driver pulley 28. As the driver pulley rotates, the holder plate 40 translates in between the grooved bearing wheels 31.

The holder plate 40 also supports a solenoid 60 at one end thereof. The holder plate 40 has a bracket 40A. A spring plate 62 is secured to the bracket 40A via rivets 63. A vibrator plate 61 is supported on top of the solenoid 60, wherein the vibrator plate is connected to the spring plate 62. In one embodiment, the solenoid 60 is connected to control PCB 70. The operation of the solenoid 60 is regulated by the control PCB 70. In one embodiment, the spring plate 62 is made of a magnetic material, e.g., carbon steel. As such, the spring plate 62 responds to the magnetic fields generated by the operation of the solenoid 60. More specifically, the spring plate 62 moves down against the solenoid 60 for each electrical pulse received by the solenoid 60 from the control PCB 70.

At the end of the holder plate 40, the holder plate 40 supports the tattoo applicator 50. The hook shaped extension 64 and the vibrator plate 61 have overlapping slots 61A, 64A that accommodate the top portion of the tattoo applicator 50. A resilient pad 57 is fitted onto the top portion of the tattoo applicator 50 at a location between the overlapping slots 61A, 64A such that the resilient pad 57 is in contact with the hook shaped extension 64.

Figures 6B, 6C:
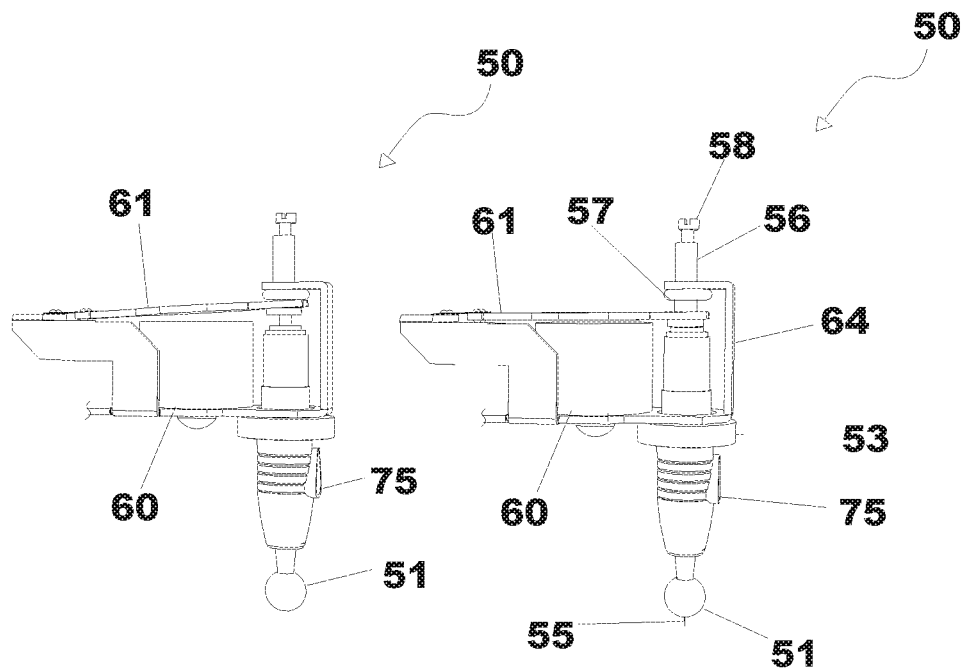
FIG. 6A thru FIG. 6C illustrate the different views of the applicator, in accordance with an embodiment of the present invention.
Figure 6A:
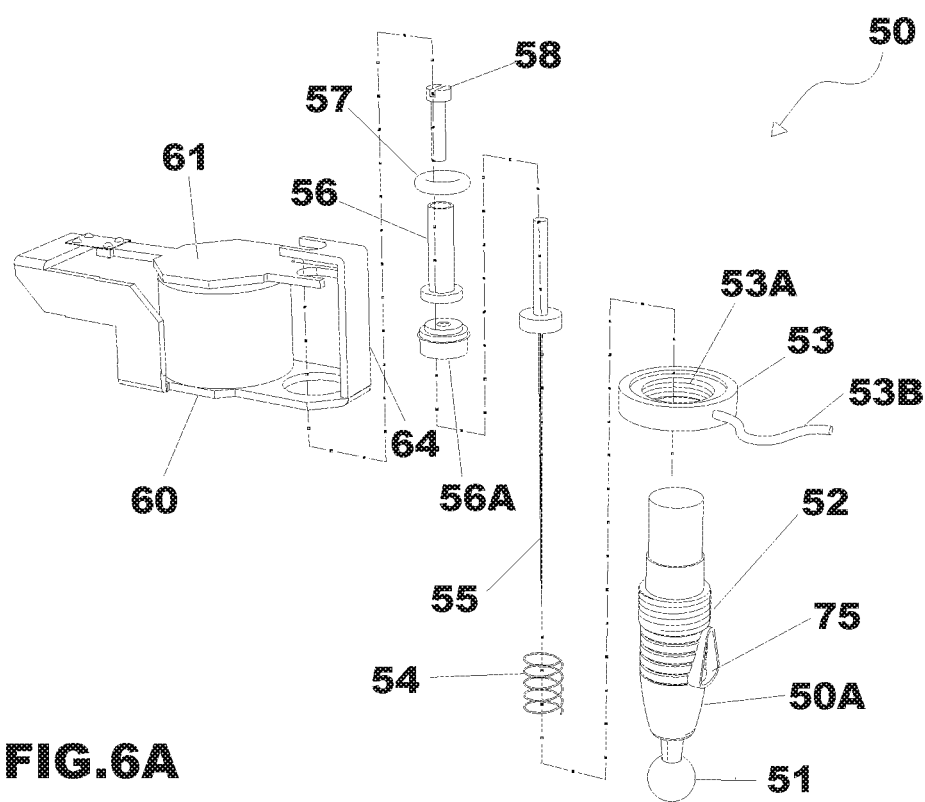

FIG. 6A thru FIG. 6C illustrate the different views of the tattoo applicator 50, in accordance with an embodiment of the present invention. Referring to FIG. 6A thru FIG. 6C, the tattoo applicator 50 comprises a needle 55. The needle 55 is fitted with a top hat sleeve 56 and a cover 56A at an operative top portion thereof. At the bottom portion of the needle 55, a biasing member 54 is placed. The bottom portion of the needle 55 along with the biasing member 54 is accommodated within a housing 50A of the tattoo applicator 50. The upper portion of the needle 55, top hat sleeve 56, and the cover 56A are supported on the housing 50A. A screw 58 fits onto the top hat sleeve 56 to secure the top hat sleeve 56, and the needle 55 on the housing 50A.

The tattoo applicator 50 further comprises a ball 51 fitted at an operative bottom end of the housing 50A. Referring to FIG. 6B, the solenoid 60 is deactivated or in an OFF position. In such a position, the needle 55 does not shows under ball 51 as the vibrator plate 61 is in contact with the resilient pad 57, and the needle 55 is lifted up inside the housing 50A as a consequence. Referring FIG. 6C, the solenoid 60 activated or in ON position attracts the vibrator plate 61, thereby pushing down the needle 55 such that the needle 55 is exposed outside the ball 51. The needle 55 is slidable inside the ball 51. The screw 58 that screws onto the top hat sleeve 56 facilitates the adjustment of the desired length by which the needle 55 can be extended out of the ball 51. More specifically, the screw 58 pushes the needle 55 or allows the retraction of the needle 55. The spring 54 constantly pushes the needle 55 up and it is only overcome when the needle 55 is pushed down due to the operation of the solenoid 60 and the attraction of the vibrator plate 61 onto the solenoid, which pushes the needle 55 down enough to overcome the biasing force of the biasing member 54 and extending out of the ball 51. The housing 50A has an opening 75 for receiving a conduit supplying the ink required for the tattoo.

In an embodiment, the tattoo applicator 50 further comprises a pressure sensor 53. The pressure sensor 53 is coupled to the control PCB 70. As the tattoo applicator 50 changes position in accordance with the movement of the base carriage 20 and the top carrier 30, the pressure acting on the tattooing area via the ball 51 and the needle 55 may vary due to gravity. Too much pressure may stretch the skin giving a distorted tattoo results or not enough pressure will affect the result. The pressure sensor 53 facilitates the maintenance of constant pressure throughout the tattooing area. More specifically, the control PCB 70 is in constant communication with the pressure sensor 53 and controls the motor 26 drive the motor 26 either to unwind or wind the torsion spring 28, thereby regulating the pressure acting on the top carrier 30, the holder plate 40, and the tattoo applicator 50.

Referring again to FIG. 1 and FIG. 2, while a tattoo session, it is often desirable to stop and raise the needle for cleaning or other reasons like patient discomfort. To this end, the machine 100 comprises a lever 73 that pivots around a pin 74. The lever 73 is are secured onto the top carrier 30 via the pin 74. In order to break the contact of the needle with the tattooing area, the user can move the lever 73, which in turn raises the top carrier 30 and the holder plate 40 away from the tattooing area. In an embodiment, the machine 100 further comprises a proximity sensor 73A disposed adjacent the pin 74. The proximity sensor 73A is coupled to the control PCB 70. When the holder plate 40 is raised using the lever 73, the proximity sensor 73A sends a signal to the control PCB 70 to pause the operation of the machine 100. The operation of the machine 100 resumes once the lever 73 is used again to bring down the holder plate 40.

In accordance with an embodiment of the present invention, the control PCB 70 connects to a computing device via wireless communication means. In another embodiment, the connection between the control PCB 70 and a computing device can be facilitated via a cable 71, which can be a USB connection in one example. The power supply for the operation machine 100 is provided via the power supply cable 72.

It is to be noted that in the conventional CNC controlled tattoo machines, the movement of the applicator along a Z-axis is typically controlled by the program fed to the machine. The position of applicator along the Z-axis is a critical parameter as it directly controls the pressure with which the needle of the applicator interacts with the skin on the tattooing area. An inaccurate input in the program may cause the applicator needle to pierce the skin more than desired, thereby injuring the user. An advantageous aspect of the hinged connection of the holder plate 40 and the top carrier 30 with the base carriage 20 is that a user can manually raise the holder plate 40 using the lever 73 in case of discomfort. The pressure acting on the tattooing area, in accordance with some embodiments of the present invention, is due to the self-weight of the holder plate 40 and the tattoo applicator 50. The ball 51 allows the tattoo applicator 50 to be rested on the tattooing area. In accordance with some embodiments of the present invention, the motor 26 and the torsion spring 28 facilitate the regulation and application of a constant pressure on the top carrier 30 and the holder plate 40, wherein the pressure can be set to be just enough to complete the tattooing operation without any injuries to the user. In an embodiment, this pressure is computed while also taking into consideration the self-weight of the top carrier 30, the holder plate 40, and the tattoo applicator 50.

Those skilled in the art will readily recognize, in light of and in accordance with the teachings of the present invention, that any of the foregoing steps and/or system modules may be suitably replaced, reordered, removed and additional steps and/or system modules may be inserted depending upon the needs of the particular application, and that the systems of the foregoing embodiments may be implemented using any of a wide variety of suitable processes and system modules, and is not limited to any particular computer hardware, software, middleware, firmware, microcode and the like. For any method steps described in the present application that can be carried out on a computing machine, a typical computer system can, when appropriately configured or designed, serve as a computer system in which those aspects of the invention may be embodied. Such computers referenced and/or described in this disclosure may be any kind of computer, either general purpose, or some specific purpose computer such as, but not limited to, a workstation, a mainframe, GPU, ASIC, etc. The programs may be written in C, or Java, Brew or any other suitable programming language. The programs may be resident on a storage medium, e.g., magnetic or optical, e.g., without limitation, the computer hard drive, a removable disk or media such as, without limitation, a memory stick or SD media, or other removable medium. The programs may also be run over a network, for example, with a server or other machine sending signals to the local machine, which allows the local machine to carry out the operations described herein.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

It is noted that according to USA law 35 USC § 112 (1), all claims must be supported by sufficient disclosure in the present patent specification, and any material known to those skilled in the art need not be explicitly disclosed. However, 35 USC § 112 (6) requires that structures corresponding to functional limitations interpreted under 35 USC § 112 (6) must be explicitly disclosed in the patent specification. Moreover, the USPTO's Examination policy of initially treating and searching prior art under the broadest interpretation of a "mean for" or "steps for" claim limitation implies that the broadest initial search on 35 USC § 112(6) (post AIA 112(f)) functional limitation would have to be conducted to support a legally valid Examination on that USPTO policy for broadest interpretation of "mean for" claims. Accordingly, the USPTO will have discovered a multiplicity of prior art documents including disclosure of specific structures and elements which are suitable to act as corresponding structures to satisfy all functional limitations in the below claims that are interpreted under 35 USC § 112(6) (post AIA 112(f)) when such corresponding structures are not explicitly disclosed in the foregoing patent specification. Therefore, for any invention element(s)/structure(s) corresponding to functional claim limitation(s), in the below claims interpreted under 35 USC § 112(6) (post AIA 112(f)), which is/are not explicitly disclosed in the foregoing patent specification, yet do exist in the patent and/or non-patent documents found during the course of USPTO searching, Applicant(s) incorporate all such functionally corresponding structures and related enabling material herein by reference for the purpose of providing explicit structures that implement the functional means claimed. Applicant(s) request(s) that fact finders during any claims construction proceedings and/or examination of patent allowability properly identify and incorporate only the portions of each of these documents discovered during the broadest interpretation search of 35 USC § 112(6) (post AIA 112(f)) limitation, which exist in at least one of the patent and/or non-patent documents found during the course of normal USPTO searching and or supplied to the USPTO during prosecution. Applicant(s) also incorporate by reference the bibliographic citation information to identify all such documents comprising functionally corresponding structures and related enabling material as listed in any PTO Form-892 or likewise any information disclosure statements (IDS) entered into the present patent application by the USPTO or Applicant(s) or any 3rd parties. Applicant(s) also reserve its right to later amend the present application to explicitly include citations to such documents and/or explicitly include the functionally corresponding structures which were incorporate by reference above.

Thus, for any invention element(s)/structure(s) corresponding to functional claim limitation(s), in the below claims, that are interpreted under 35 USC § 112(6) (post AIA 112(f)), which is/are not explicitly disclosed in the foregoing patent specification, Applicant(s) have explicitly prescribed which documents and material to include the otherwise missing disclosure, and have prescribed exactly which portions of such patent and/or non-patent documents should be incorporated by such reference for the purpose of satisfying the disclosure requirements of 35 USC § 112 (6). Applicant(s) note that all the identified documents above which are incorporated by reference to satisfy 35 USC § 112 (6) necessarily have a filing and/or publication date prior to that of the instant application, and thus are valid prior documents to incorporated by reference in the instant application.

Having fully described at least one embodiment of the present invention, other equivalent or alternative methods of implementing a CNC controlled tattoo machine according to the present invention will be apparent to those skilled in the art. Various aspects of the invention have been described above by way of illustration, and the specific embodiments disclosed are not intended to limit the invention to the particular forms disclosed. The particular implementation of the CNC controlled tattoo machine may vary depending upon the particular context or application. By way of example, and not limitation, the CNC controlled tattoo machine described in the foregoing were principally directed to applying tattoos while using motors only to control the movement of the applicator along X and Y axes, while the movement along the Z axis was manually controlled to mitigate the risk of injuries to the user; however, similar techniques may instead be applied to artificial hair transplant, which implementations of the present invention are contemplated as within the scope of the present invention. The invention is thus to cover all modifications, equivalents, and alternatives falling within the spirit and scope of the following claims. It is to be further understood that not all of the disclosed embodiments in the foregoing specification will necessarily satisfy or achieve each of the objects, advantages, or improvements described in the foregoing specification.

Claim elements and steps herein may have been numbered and/or lettered solely as an aid in readability and understanding. Any such numbering and lettering in itself is not intended to and should not be taken to indicate the ordering of elements and/or steps in the claims.

The corresponding structures, materials, acts, and equivalents of all means or step plus function elements in the claims below are intended to include any structure, material, or act for performing the function in combination with other claimed elements as specifically claimed.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The Abstract is provided to comply with 37 C.F.R. Section 1.72(b) requiring an abstract that will allow the reader to ascertain the nature and gist of the technical disclosure. That is, the Abstract is provided merely to introduce certain concepts and not to identify any key or essential features of the claimed subject matter. It is submitted with the understanding that it will not be used to limit or interpret the scope or meaning of the claims.

The following claims are hereby incorporated into the detailed description, with each claim standing on its own as a separate embodiment.

Only those claims which employ the words "means for" or "steps for" are to be interpreted under 35 USC 112, sixth paragraph (pre-AIA) or 35 USC 112(f) post-AIA. Otherwise, no limitations from the specification are to be read into any claims, unless those limitations are expressly included in the claims.

What is claimed is:

1. A tattoo machine comprising:
   at least one brace for supporting said machine on a body part;
   a base carriage supported on said brace, said base carriage being displaceable along a length of said brace by means of a first plurality of bearing wheels affixed to said base carriage, said first plurality of bearing wheels abutting said brace, thereby supporting said base carriage on said brace;
   a top carrier coupled to said base carriage;
   a holder plate comprising a free end and a non-free end, said holder plate displaceably coupled to said top carrier, wherein the displacement of said holder plate within said top carrier is facilitated in a direction along the length of said holder plate via a second plurality of bearing wheels, and wherein a movement of said top carrier with respect to said base carriage facilitates the movement of said holder plate with respect to said base carriage;
   a lever coupled to said top carrier for raising and lowering of said top carrier and said holder plate in relation with said base carriage during a course of a tattoo application; and
   a tattoo applicator supported at said free end of said holder plate, said tattoo applicator comprising a ball for housing a tip of a needle.

2. The tattoo machine according to claim 1, further comprising a control device.

3. The tattoo machine according to claim 2, further comprising:
   a first motor coupled to said control device;
   a first driving pulley and a first idler pulley secured on said base carriage, wherein said first driving pulley is coupled to said first motor; and a driving cable disposed on said brace, wherein ends of said driving cable are secured near ends of said brace via at least one fastener, said cable being wrapped around said driving pulley and said idler pulley.

4. The tattoo machine according to claim 2, further comprising:
a second motor disposed on said top carrier and coupled to said control device;
a second driving pulley and a second idler pulley disposed on said holder plate, wherein said second driving pulley is coupled to said second motor; and
a driving cable disposed on said holder plate, wherein ends of said driving cable are secured near said ends of said holder plate via at least one fastener, said cable being wrapped around said driving pulley and said idler pulley.

5. The tattoo machine according to claim 2, further comprising:
a third motor disposed on said base carriage and coupled to said control device;
a shaft coupled to said third motor, wherein said shaft is fitted between said top carrier and said base carriage for facilitating hingeable connection therebetween; and
a torsion spring supported on said base carriage, wherein one end of said torsion spring is connected to said shaft, and an other end of said torsion spring is connected to said top carrier.

6. The tattoo machine according to claim 2, further comprising:
a solenoid disposed adjacent said free end of said holder plate;
a bracket configured on said holder plate proximal said solenoid;
a vibrator plate coupled to said bracket via a spring plate and supported on top said solenoid; and
a hook shaped extension extending from the free end of said holder plate, wherein said tattoo applicator is supported on said free end of said holder plate such that a portion of said tattoo applicator is sandwiched between said vibrator plate and said hook shaped extension.

7. The machine as claimed in claim 6, wherein said brace and said holder plate are configured to be operable for facilitating movement of said tattoo applicator along two mutually perpendicular axes.

8. The tattoo machine according to claim 1, further comprising a cushioning pad that is in engagement with said brace.

9. The tattoo machine according to claim 1, wherein said brace comprises at least one or more loops defined at first and second end of the brace.

10. The tattoo machine according to claim 9, wherein a strap engages said loops for facilitating the strapping on a body part.

11. The tattoo machine as claimed in claim 1, wherein said brace and said holder plate are configured to be operable for facilitating movement of said tattoo applicator along two mutually perpendicular axes.

12. A machine comprising:
a control device;
at least one brace for supporting said machine on a body part;
a base carriage supported on said brace, said base carriage being displaceable along a length of said brace by means of a first plurality of bearing wheels affixed to said base carriage, said first plurality of bearing wheels abutting said brace, thereby supporting said base carriage on said brace;
a top carrier hingeably coupled to said base carriage;
a holder plate displaceably coupled to said top carrier, wherein the displacement of said holder plate within said top carrier is facilitated in a direction along the length of said holder plate via a second plurality of bearing wheels, and wherein a hingeable movement of said top carrier with respect to said base carriage facilitates the hingeable movement of said holder plate with respect to said base carriage;
a lever coupled to said top carrier for raising and lowering of said top carrier and said holder plate in hingeable relation with said base carriage during a course of a tattoo application; and
a tattoo applicator supported at a free end of said holder plate, said tattoo applicator comprising a ball for housing a tip of a needle.

13. The machine according to claim 12, further comprising:
a first motor disposed on said base carriage, wherein said first motor is coupled to said control device;
a first driving pulley and a first idler pulley secured on said base carriage, wherein said first driving pulley is coupled to said first motor; and
a driving cable disposed on said brace, wherein ends of said driving cable are secured near ends of said brace via at least one fastener, said cable being wrapped around said driving pulley and said idler pulley.

14. The machine according to claim 12, further comprising:
a second motor coupled to said control device;
a second driving pulley coupled to said second motor; and
a driving cable secured to said holder plate via at least one fastener, said cable being wrapped around said second driving pulley and said second idler pulley.

15. The machine according to claim 12, further comprising:
a third motor disposed on said base carriage and coupled to said control device;
a shaft coupled to said third motor, wherein said shaft is fitted between said top carrier and said base carriage for facilitating hingeable connection therebetween; and
a torsion spring supported on said base carriage, wherein one end of said torsion spring is connected to said shaft, and an other end of said torsion spring is connected said top carrier.

16. The machine according to claim 12, further comprising a cushioning pad coupled to said brace.

17. The machine according to claim 12, wherein said brace defines at least one or more loops at a first and/or second end of the brace.

18. The machine according to claim 17, wherein a strap engages said loops for facilitating the strapping on a body part.

19. The machine according to claim 12, further comprising:
a solenoid disposed adjacent the free end of said holder plate;
a bracket configured on said holder plate proximal said solenoid;
a vibrator plate coupled to said bracket via a spring plate and supported on top said solenoid; and
a hook shaped extension extending from the free end of said holder plate, wherein said tattoo applicator is supported on said free end of said holder plate such that a portion of said tattoo applicator is sandwiched between said vibrator plate and said hook shaped extension.

20. A machine comprising:

at least one brace for supporting said machine on a body part;

a cushioning pad coupled to said brace;

a base carriage supported on said brace, said base carriage being displaceable along a length of said brace by means of a first plurality of bearing wheels affixed to said base carriage, said first plurality of bearing wheels abutting said brace, thereby supporting said base carriage on said brace;

a first motor disposed on said base carriage;

a first driving pulley and a first idler pulley secured on said base carriage, wherein said first driving pulley is coupled to said first motor;

a top carrier hingeably coupled to said base carriage;

a holder plate displaceably coupled to said top carrier, wherein the displacement of said holder plate within said top carrier is facilitated in a direction along the length of said holder plate via a second plurality of bearing wheels, and wherein a hingeable movement of said top carrier with respect to said base carriage facilitates the hingeable movement of said holder plate with respect to said base carriage;

a second motor disposed on said top carrier;

a second driving pulley and a second idler pulley disposed on said holder plate, wherein said second driving pulley is coupled to said second motor;

a driving cable disposed on said holder plate;

a third motor disposed on said base carriage;

a shaft coupled to said third motor a torsion spring supported on said base carriages;

a lever coupled to said top carrier for raising and lowering of said top carrier and said holder plate in hingeable relation with said base carriage during a course of a tattoo application; and a tattoo applicator supported at a free end of said holder plate, said tattoo applicator comprising a ball for housing a tip of a needle.

* * * * *